United States Patent [19]

Kronauge et al.

[11] Patent Number: 4,481,184

[45] Date of Patent: Nov. 6, 1984

[54] CATIONIC TECHNETIUM (I) COMPLEXES

[75] Inventors: James F. Kronauge, Plainsboro, N.J.; Kenneth A. Glavan, Toledo, Ohio

[73] Assignee: E. R. Squibb & Sons, Inc., Princeton, N.J.

[21] Appl. No.: 465,957

[22] Filed: Feb. 14, 1983

[51] Int. Cl.$^3$ .................... A61K 29/00; A61K 49/00
[52] U.S. Cl. .................... 424/1.1; 260/429 J; 260/440; 424/9
[58] Field of Search .................... 260/429 J, 440; 424/1.1, 9

[56] References Cited

U.S. PATENT DOCUMENTS 4,387,087 6/1983 Deutsch et al. .................... 424/1.5

FOREIGN PATENT DOCUMENTS 0038756 4/1981 European Pat. Off. .

OTHER PUBLICATIONS

J. Nucl. Med., vol. 23, No. 5, "Radiopharmaceutical Chemistry II: Technetium", Fritzberg and Jones, pp. 16–17.

Jülich, Aug. 23–27, 1982, *Fourth International Symposium on Radiopharmaceutical Chemistry*, "The Chemistry of Technetium", pp. 318–321.

*Primary Examiner*—Christine M. Nucker
*Attorney, Agent, or Firm*—Lawrence S. Levinson; Donald J. Barrack

[57] ABSTRACT

Myocardial perfusion can be measured and ischemia and infarction can be diagnosed using compounds having the formula

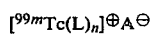

$[^{99m}Tc(L)_n]^{\oplus} A^{\ominus}$ wherein
A is an anion;
n is 1, 2, 3 or 6;
if n is 1, L is a hexadentate ligand, if n is 2, L is a tridentate ligand, if n is 3, L is a monodentate ligand.

17 Claims, No Drawings

CATIONIC TECHNETIUM (I) COMPLEXES

RELATED APPLICATION

U.S. patent application Ser. No. 392,811, filed June 28, 1982, now U.S. Pat. No. 4,374,821, issued Feb. 22, 1983 discloses myocardial imaging agents having the structure

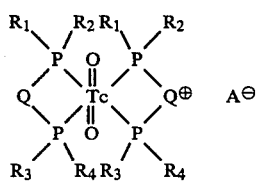

wherein Q is a $-(CH_2)_n-$ linking group wherein n is 2 to 8, and preferably 2 to 5, or Q is a 1,2-phenylene group

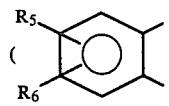

wherein $R_5$ and $R_6$ are independently selected from hydrogen, lower alkyl, or halogen) and $R_1$, $R_2$, $R_3$ and $R_4$ are independently the same or different and are hydrogen, lower alkyl, or phenyl, and A represents an anion group; the technetium is in an oxidation state of +5.

BACKGROUND OF THE INVENTION

European patent application No. 0038756 to Deutsch and Glavan discloses cationic lipophilic complexes of technetium-99m that are useful as negative heart imaging agents in that they accumulate in the normal heart and visualize an infarct as a cold area on a relatively hot background of normal tissue.

The subject complexes of technetium-99m have lipophilic ligands and an overall cationic charge and are described by the formula $$[(L)_2{}^{99m}Tc(X)_2]^{\oplus}X^{\ominus},$$

wherein each L represents the same or different lipophilic ligand strongly chelating for a technetium-99m cation, and wherein the three X's are the same or different monovalent anionic ligand. Examples of such complexes include 99m-Tc(diars)$_2$X$_2$+ wherein diars is o—C$_6$H$_4$(As(CH$_3$)$_2$)$_2$ (o-phenylenebis(dimethylarsine)) and X is Cl or Br, trans-99m-Tc(dmpe)$_2$Cl$_2$+ (wherein dmpe is (CH$_3$)$_2$P—CH$_2$CH$_2$—P(CH$_3$)$_2$) which is said to be the preferred myocardial imaging agent and 99m-Tc(tetraphos)Cl$_2$+ (wherein tetraphos is P(CH$_2$CH$_2$P(C$_6$H$_5$)$_2$)$_3$). The technetium in these complexes is in an oxidation state of +3.

In two abstracts (J. Nucl. Med., 23(5): P16–P17 and Jülich, Aug. 23–27, 1982, pgs 319–320), Jones et al disclose a class of technetium complexes containing various isonitrile ligands; the technetium in these complexes is in an oxidation state of +1. The compounds are useful as negative heart imaging agents.

Lock, in an abstract dealing with the chemistry of technetium (Jülich, Aug. 23–27, 1982, pg 318) mentions technetium in the +1 oxidation state.

BRIEF DESCRIPTION OF THE INVENTION

The complexes of this invention are useful for measuring myocardial perfusion or the diagnosis of ischemia and infarction and can be represented by the general formula $$[^{99m}Tc(L)_n]^{\oplus}A^{\ominus} \qquad \text{I}$$

wherein
A is an anion;
n is 1, 2, 3 or 6;
if n is 1, L is a hexadentate ligand having the formula

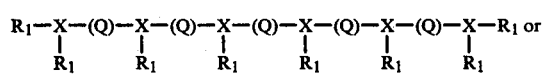

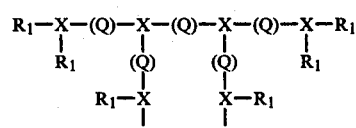

if n is 2, L is a tridentate ligand having the formula

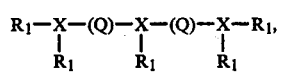

if n is 3, L is a bidentate ligand having the formula

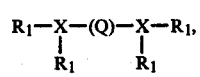

and if n is 6, L is a monodentate ligand having the formula

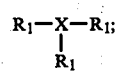

wherein X is phosphorus or arsenic, the $R_1$ groups are the same or different alkyl or aryl groups, each Q is independently a $-(CH_2)_m-$ group or

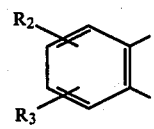

m is 1, 2 or 3 and $R_2$ and $R_3$ are the same or different and each is hydrogen, alkyl, or halogen.

The term "aryl", as used throughout the specification, refers to phenyl and phenyl substituted with 1, 2 or 3 alkyl or halogen groups.

The term "alky" as used throughout the specification, refers to alkyl groups having 1 to 4 carbon atoms. This includes methyl, ethyl, n-propyl, isopropyl, n-butyl, isobutyl, and t-butyl.

The term "halogen" refers to fluorine, chlorine, bromine and iodine.

The term "anion" refers to any pharmaceutically acceptable anion. The halogens, perchlorate (ClO$_4$—), hexafluorophosphate (PF$_6$—), tetrafluoroborate (BF$_4$—) and thiocyanate (SCN—) are exemplary.

DETAILED DESCRIPTION OF THE INVENTION

The complexes of this invention can be obtained using technetium-99m in the form of its pertechnetate ion, the form obtained from commercially available technetium-99m parent-daughter generators; such technetium is in an oxidation state of +7. The generation of the pertechnetate ion using this type of generator is described in more detail in U.S. Pat. Nos. 3,369,121 and 3,920,995. These generators are usually eluted with saline solution, and the pertechnetate ion is obtained as the sodium salt.

To prepare the complexes of this invention, pertechnetate ion (in the form of a salt) is reduced by heating in the presence of a liquid (L). The reduction can be carried out in the presence of a chemical reducing agent, e.g., sodium borohydride, stannous chloride, or sodium hyposulfite. The solvent system used for the reaction is not critical; methanol, ethanol or a combination of either with water is preferred. If a chemical reducing agent (other than the ligand) is not present, the reaction will preferably be carried out in a pressure vessel at a temperature greater than about 100° C. If an added chemical reducing agent is used, the reaction will preferably be run under reflux conditions.

In addition to pertechnetate, ligand, chemical reducing agent (optional) and solvent, the reaction mixture will also contain the anion "A" in the form of a salt.

In carrying out the above described reduction reaction the molar ratio of ligand (L) to pertechnetate ion should be not less than about 6:1. The larger the excess of ligand used, the more carrier-free the product. The concentration of anion (A) is not critical. However, the anion will preferably be chlorine, present as sodium chloride in an amount sufficient to provide an isotonic concentration of 0.15 molar after the pertechnetate ion has been added.

The complexes of this invention can be used to measure myocardial perfusion and for the diagnosis of ischemia and infarction. To utilize a compound of formula I, it is first dissolved or suspended in pharmaceutically acceptable medium for administration (e.g., saline or mixtures of saline and ethanol, propylene glycol, or glycerol; or aqueous media). The formulation can also contain various adjuvants including preservatives, such as alkyl parabens (e.g., methyl paraben and propyl paraben), and solubilizing agents (e.g., polyvinylpyrrolidone, ethylene glycol distearate, glycol and phenylsalicyclic acid). Imaging of the myocardium can be carried out using standard scanning techniques; see, for example, Andres, J. F. et al., *Nuclear Medicine*, Wiley & Sons, New York, 1977.

The following examples are specific embodiments of this invention.

EXAMPLE 1

Technetium(I)tris[bis(1,2-dimethylphosphino)ethane]-perchlorate

Ammonium pertechnetate (21.33 m), lithium perchlorate (16.18 mg) and methanol (1.0 ml) were placed into a 2-necked 10 ml round bottom flask equipped with a water-cooled condenser, inlet-outlet tubes and stir bar. The apparatus was flushed with nitrogen, and bis(1,2-dimethylphosphino)ethane (1.0 ml) was added to the flask. The reaction mixture was refluxed for 2 hours, and then sodium borohydride (ca. 5 mg.) was added to the flask. After an additional 2 hours of refluxing, the condenser was removed and the solution was allowed to go to dryness by heating. The resulting solid was dissolved in methanol, filtered to remove the resultant precipitate, and concentrated in vacuo to yield the title compound. After cooling to room temperature, the product was recrystallized from a warm methanol/water mixture.

EXAMPLE 2

Technetium(I)tris[bis(1,2-dimethylphosphino)ethane]-phosphorous hexafluoride salt

Method I

Technetium(I)tris[bis(1,2-dimethylphosphino)ethane]perchlorate was dissolved in methanol and lithium phosphorous hexafluoride was added, yielding the title compound, which was recrystallized from a warm methanol/water mixture.

Method II

Ammonium pertechnetate (150.27 mg), sodium phosphorous hexafluoride (ca. 20 mg), 95% ethanol (20 ml), and water (5 ml) were added to a 50 ml 3-neck flask equipped with a condenser. The solution was stirred with a magnetic stir bar while nitrogen was blown over the mixture for about 30 minutes. bis[(1,2-Dimethylphosphino)ethane] (3.5 ml) was injected from a glass syringe through a serum septum, and the solution was heated for about 2 hours. About 100 mg of sodium borohydride was added and heating was continued for about 4 hours. The condenser was disconnected and the solution allowed to evaporate to near dryness. Methanol (30 ml) was added and stirring was continued without heating. The solution was filtered through a fritted glass filter, and about 20 ml of water was added to the filtrate. The solution was condensed on a hot plate, and upon cooling and the addition of about 20 mg of additional sodium phosphorous hexafluoride a precipitate formed. The precipitate was collected and recrystallized from hot methanol/water slowly to yield crystalline product.

EXAMPLE 3

Technetium(I)tris[bis(1,2-Dimethylphosphino)ethane]-fluoride

Ammonium pertechnetate (150.47 mg), sodium fluoride (0.3422 g), and absolute ethanol (30 ml) were placed into a 50 ml 3-necked round bottom flask equipped with a water-cooled condenser and stir bar. The apparatus was flushed with nitrogen for 30 minutes and then bis[(1,2-dimethylphosphino)ethane] (2.5 ml) was added. The reaction mixture was refluxed for 4 hours and sodium borohydride was added. The mixture was refluxed for an additional 2 hours, the condenser was removed and the solution was allowed to concentrate to dryness under heat. The resulting solid was dissolved in methanol, filtered to remove an insoluble precipitate, and the filtrate concentrated, under vacuum, to dryness, yielding the title product.

EXAMPLE 4

Technetium(I)tris[bis(1,2-Dimethylphosphino)ethane]-bromide bis[(1,2-Dimethylphosphino)ethane] (300 μl), 95% ethanol (570 μl), 1N hydrogen bromide (50 μl), and sodium pertechnetate (200 µl) were added to a serum vial and heated to 130° C. for 60 minutes, allowed to cool to room temperature and diluted with 1.0 ml of 0.15N saline and 3 ml of sterile water. The mixture was filtered through a hydrophobic 0.2 micron sterile filter to obtain the product used for the biodistribution studies reported below.

Biodistribution Data for Technetium(I)tris[bis(1,2-Dimethylphosphino)ethane]-bromide Male Sprague-Dawley rats (200–300 g) were allowed food and water ad libitum. The dose of test compound (0.10 ml of a 0.10 mCi/ml solution) was administered via the external jugular vein under ether anaesthesia. At each time point of 5, 20, 60 and 180 minutes post injection the four rats were re-anaesthetized with ether, a blood sample was withdrawn from the aorta and the heart, lungs, liver, kidneys, spleen, femoral bone, muscle, thyroid, brain and adrenals were dissected out. The tissues were weighed and then counted in a Nuclear Chicago auto gamma spectrophotometer with the appropriate-volume corrected-standards to enable the results to be expressed as percent injected dose per organ and percent injected dose of tissue. The heart to tissue ratios were calculated on a per gram basis for blood, lungs and liver.

The results are reported below. Each point is an average of four animals ± one standard deviation.

| Percent Injected Dose per Organ | | | |
|---|---|---|---|
| | Heart | Lungs | Liver |
| 5 min. | 1.55% ± .16 | 2.42% ± .37 | 16.26% ± 1.62 |
| 20 min. | 1.30% ± .14 | 1.65% ± .22 | 14.68% ± 2.17 |
| 60 min. | 1.45% ± .27 | 1.41% ± .49 | 13.36% ± 1.88 |
| 180 min. | 1.19% ± .24 | 1.24% ± .39 | 9.28% ± 1.76 |

| Percent Injected Dose per gram of Tissue | | | | |
|---|---|---|---|---|
| | Heart | Blood | Lungs | Liver |
| 5 min. | 1.72% ± .21 | .21 ± .03 | 1.78 ± .22 | 1.45 ± .17 |
| 20 min. | 1.57% ± .11 | .14 ± .05 | 1.20 ± .13 | 1.31 ± .17 |
| 60 min. | 1.84% ± .42 | .09 ± .01 | .85 ± .29 | 1.40 ± .25 |
| 180 min. | 1.47% ± .24 | .04 ± .006 | .94 ± .36 | .93 ± .10 |

| Heart/organ Ratios for Determining Image Quality-Contrast | | | |
|---|---|---|---|
| | Heart/Blood | Heart/Lung | Heart/Liver |
| 5 min. | 8.2 | .97 | 1.2 |
| 20 min. | 11.2 | 1.30 | 1.2 |
| 60 min. | 20.4 | 2.20 | 1.3 |
| 180 min. | 36.8 | 1.56 | 1.6 |

What is claimed is:

1. A complex having the formula $$[^{99m}Tc(L)_n]^{\oplus}A^{\ominus}$$

wherein
A is an anion;
n is 1, 2, 3 or 6;
if n is 1, L is a hexadentate ligand having the formula

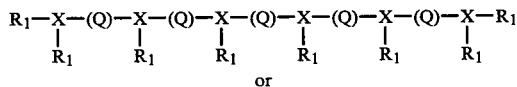

or

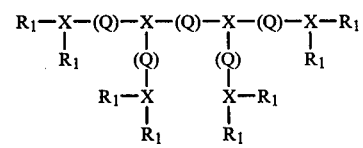

if n is 2, L is a tridentate ligand having the formula

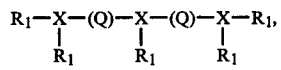

if n is 3, L is a bidentate ligand having the formula

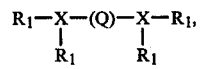

and if n is 6, L is a monodentate ligand having the formula

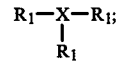

wherein X is phosphorus or arsenic, the $R_1$ groups are the same or different alkyl or aryl groups, each Q is independently a $-(CH_2)_m-$ group or

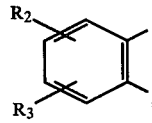

m is 1, 2 or 3 and $R_2$ and $R_3$ are the same or different and each is hydrogen, alkyl, or halogen.

2. A complex in accordance with claim 1 wherein n is 3 and L is a ligand having the formula

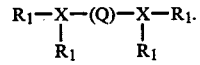

3. A complex in accordance with claim 2 wherein Q is $-(CH_2)_m-$.

4. A complex in accordance with claim 3 wherein m is 2.

5. A complex in accordance with claim 2 wherein Q is

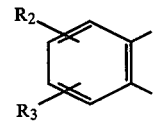

6. A complex in accordance with claim 2 wherein each $R_1$ group is methyl and Q is $-(CH_2)_2-$.

7. A complex in accordance with claim 1 wherein n is 6 and L is a ligand having the formula

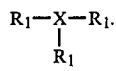

8. A compound in accordance with claim 7 wherein each $R_1$ group is methyl.

9. A compound in accordance with claim 1 wherein n is 2 and L is a ligand having the formula

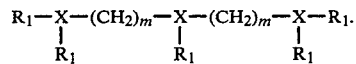

10. A compound in accordance with claim 9 wherein each $R_1$ group is methyl and m is 2.

11. A compound in accordance with claim 9 wherein each $R_1$ group is methyl and m is 3.

12. A compound in accordance with claim 1 wherein n is 1 and L is a ligand having the formula

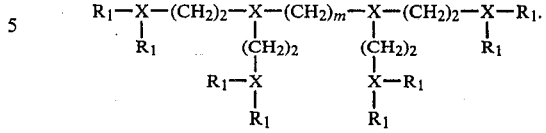

13. A compound in accordance with claim 12 wherein each $R_1$ group is methyl and m is 2.

14. A compound in accordance with claim 12 wherein each $R_1$ group is methyl and m is 3.

15. A compound in accordance with claim 1 wherein n is 1 and L is a ligand having the formula

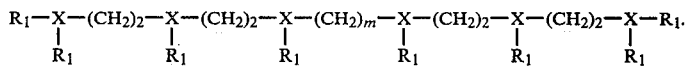

16. A compound in accordance with claim 15 wherein each $R_1$ group is methyl and m is 2.

17. A compound in accordance with claim 15 wherein each $R_1$ group is methyl and m is 3.

* * * * *

UNITED STATES PATENT AND TRADEMARK OFFICE
CERTIFICATE OF CORRECTION

PATENT NO. : 4,481,184

DATED : November 6, 1984

INVENTOR(S) : James F. Kronauge et al.

It is certified that error appears in the above—identified patent and that said Letters Patent is hereby corrected as shown below:

Column 2, line 61, delete "alky" and replace with --alkyl--.
Column 7, line 6, delete "compound" and replace with --complex--.
Column 7, line 8, delete "compound" and replace with --complex--.
Column 7, line 15, delete "compound" and replace with --complex--.
Column 7, line 25, delete "compound" and replace with --complex--.
Column 8, line 1, delete "compound" and replace with --complex--.
Column 8, line 11, delete "compound" and replace with --complex--.
Column 8, line 13, delete "compound" and replace with --complex--.

UNITED STATES PATENT AND TRADEMARK OFFICE
CERTIFICATE OF CORRECTION

PATENT NO. : 4,481,184
DATED : November 6, 1984
INVENTOR(S) : James F. Kronauge et al.

It is certified that error appears in the above—identified patent and that said Letters Patent is hereby corrected as shown below:

Column 8, line 15, delete "compound" and replace with --complex--.
       Column 8, line 22, delete "compound" and replace with --complex--.
       Column 8, line 24, delete "compound" and replace with --complex--.

Signed and Sealed this

Thirtieth Day of April 1985

[SEAL]

Attest:

DONALD J. QUIGG

*Attesting Officer*     *Acting Commissioner of Patents and Trademarks*